US009308521B2

(12) United States Patent
Cooper et al.

(10) Patent No.: US 9,308,521 B2
(45) Date of Patent: Apr. 12, 2016

(54) ZEOLITE Y

(71) Applicant: PQ CORPORATION, Malvern, PA (US)

(72) Inventors: David Allen Cooper, Morrisville, PA (US); Cornelius Ouwehand, Purmerend (NL); Laszlo Domokos, Hoofddorp (NL); Lay Hwa Ong, Senja Link (SG)

(73) Assignee: PQ CORPORATION, Malvern, PA (US)

( * ) Notice: Subject to any disclaimer, the term of this patent is extended or adjusted under 35 U.S.C. 154(b) by 322 days.

(21) Appl. No.: 14/157,022

(22) Filed: Jan. 16, 2014

(65) Prior Publication Data
US 2014/0135560 A1 May 15, 2014

Related U.S. Application Data

(63) Continuation of application No. 12/768,969, filed on Apr. 28, 2010, now abandoned.

(60) Provisional application No. 61/173,698, filed on Apr. 29, 2009.

(51) Int. Cl.
C01B 39/02 (2006.01)
B01J 20/18 (2006.01)
B01J 20/30 (2006.01)
C01B 39/24 (2006.01)
C07C 7/13 (2006.01)

(52) U.S. Cl.
CPC ............ B01J 20/3078 (2013.01); B01J 20/186 (2013.01); C01B 39/026 (2013.01); C01B 39/24 (2013.01); C07C 7/13 (2013.01); B01J 2229/36 (2013.01)

(58) Field of Classification Search
CPC ........ C07C 7/13; C01B 39/026; C01B 29/24; B01J 20/186; B01J 20/3078; B01J 2229/36
See application file for complete search history.

(56) References Cited

U.S. PATENT DOCUMENTS

| 3,130,007 | A | 4/1964 | Breck | |
|---|---|---|---|---|
| 4,085,069 | A | 4/1978 | Alafandi et al. | |
| 4,331,694 | A | 5/1982 | Izod | |
| 5,059,567 | A * | 10/1991 | Linsten | B01J 37/30 423/112 |
| 5,240,889 | A * | 8/1993 | West | B01J 29/084 502/202 |
| 5,316,993 | A * | 5/1994 | Sextl | B01D 53/02 502/64 |
| 5,435,987 | A | 7/1995 | Cooper | |
| 6,284,218 | B1 | 9/2001 | Kuvettu et al. | |
| 6,521,208 | B1 * | 2/2003 | Cooper | B01J 20/18 423/713 |
| 7,192,900 | B2 | 3/2007 | Creyghton et al. | |
| 2002/0094931 | A1 | 7/2002 | Wang et al. | |
| 2004/0138051 | A1 | 7/2004 | Shan et al. | |
| 2008/0183025 | A1 | 7/2008 | Van Broekhoven et al. | |
| 2011/0251049 | A1 | 10/2011 | Kuroda et al. | |

FOREIGN PATENT DOCUMENTS

| CN | 1068977 A | 2/1993 |
|---|---|---|
| CN | 1342132 A | 3/2002 |
| CN | 1717277 A | 1/2006 |
| EP | 0140608 A1 | 5/1985 |
| EP | 0247678 A2 | 12/1987 |
| EP | 0247679 A2 | 12/1987 |
| JP | S56022624 A | 2/1981 |
| JP | S5714132 A | 1/1982 |
| JP | H05138016 A | 6/1993 |
| JP | H05178610 A | 7/1993 |
| JP | 2002191973 A | 7/2002 |
| JP | 2002526237 A | 8/2002 |
| JP | 2002538069 A | 11/2002 |
| JP | 2006505676 A | 2/2006 |
| JP | 2006507923 A | 3/2006 |
| WO | 2004044098 A1 | 5/2004 |
| WO | 2004047988 A1 | 6/2004 |
| WO | 2004050548 A2 | 6/2004 |
| WO | 2005084799 A1 | 9/2005 |

OTHER PUBLICATIONS

International Search Report and Written Opinion of the International Searching Authority for PCT/US2010/032691 dated Jun. 29, 2010.
International Preliminary Report on Patentability for PCT/US2010/032691 dated May 30, 2011 (Form PCT/IPEA/409).
Chinese Office Action and Search Report dated Feb. 21, 2013.
Hughes, Thomas Robert, et al. "A Study of the Surface Structure of Decationized Y Zeolite by Quantitative Infrared Spectroscopy," The Journal of Physical Chemistry, vol. 71, No. 7, pp. 2192-2201, Jun. 1, 1967.

(Continued)

Primary Examiner — David M Brunsman
(74) Attorney, Agent, or Firm — Buchanan Ingersoll & Rooney PC

(57) ABSTRACT

Process for preparing a modified zeolite Y which process comprises subjecting zeolite Y having a silica to alumina molar ratio of at least 10 to calcination at a temperature of from 700 to 1000° C. wherein (i) the steam partial pressure is at most 0.06 bar at a temperature of from 700 to 800° C., (ii) the steam partial pressure is at most 0.08 bar at a temperature of from 800 to 850° C., (iii) the steam partial pressure is at least 0.03 bar at a temperature of from 850 to 900° C., and (iv) the steam partial pressure is at least 0.05 bar at a temperature of from 900 to 950° C. and (v) the steam partial pressure is at least 0.07 bar at a temperature of from 950 to 1000° C., a modified zeolite Y obtainable by such process, zeolite Y having a silica to alumina molar ratio of at least 10, the infrared spectrum of which has a peak at 3700 $cm^{-1}$ but substantially no peaks at 3605 and 3670 $cm^{-1}$ and zeolite Y having a silica to alumina molar ratio of at least 10, which zeolite Y has an acidity as measured by exchange with perdeuterated benzene of at most 20 micromole/gram.

23 Claims, No Drawings

(56) References Cited

OTHER PUBLICATIONS

Makarova, M.A., "Bronsted acidity in US-Y zeolites," Studies in Surface Science and Catalysis; Zeolites and Related Microporous Materials: State of the Art 1994: Proceedings of the 10th International Zeolite Conference, Elsevier B.V., NL; Garmisch Partenkirchen, Germany, vol. 84, No. Part A, pp. 365-372. Jan. 1, 1994.
European Search Report for PCT/US2010032691 dated Dec. 20, 2013.
Japanese Office Action dated Sep. 17, 2015 for Japanese Patent Application No. 2012-508624.
Borade et al., Acid Sites in Dehydroxylated Y Zeolites: An X-Ray Photoelectron and Infrared Spectroscopic Study using Pyridine as a Probe Molecule, J.Chem. Soc. Faraday Trans., 1990, 86(23), 3949-3956.
Japanese Office Action dated Feb. 19, 2015 for Japanese Patent Application No. 2012-508624.
Japanese Office Action dated May 22, 2014 for Japanese Patent Application No. 2012-508624.

* cited by examiner

ZEOLITE Y

CROSS-REFERENCE TO RELATED APPLICATION

This application is a continuation application of U.S. Utility patent application Ser. No. 12/768,969 filed Apr. 28, 2010 which claims priority to U.S. Provisional Patent Application No. 61/173,698 filed Apr. 29, 2009. The documents are incorporated by reference herein, The present invention relates to modified zeolite Y and to a process for preparing such zeolite Y.

Zeolite Y is a well-known zeolite form and has a wide range of documented uses as catalyst supports, adsorbents, selective separation materials, etc. in the petrochemical and chemical industries and also as pollution control materials for industrial, domestic and automotive use. Zeolite Y, for example, is one of the main zeolitic materials proposed for hydrocracking use. Early findings showed that modification of the basic materials described in U.S. Pat. No. 3,130,007 to produce a lowering of the unit cell size, gave improved selectivity to the desired middle distillate, or mid-barrel, products.

It has now surprisingly been found that a specific kind of zeolite Y easily can be treated to obtain zeolite Y having modified properties. It was found possible to reduce the acidity of zeolite Y thereby.

Accordingly, the present invention provides a process for preparing a zeolite Y having a silica to alumina molar ratio of at least 10 to calcination at a temperature of from 700 to 1000° C. wherein (i) the steam partial pressure is at most 0.06 bar at a temperature of from 700 to 800° C., (ii) the steam partial pressure is at most 0.08 bar at a temperature of from 800 to 850° C., (iii) the steam partial pressure is at least 0.03 bar at a temperature of from 850 to 900° C., and (iv) the steam partial pressure is at least 0.05 bar at a temperature of from 900 to 950° C. and (v) the steam partial pressure is at least 0.07 bar at a temperature of from 950 to 1000° C. Furthermore, the present invention relates to zeolite Y obtainable by such process.

Prior art documents such as WO-A-2004/047988 and WO-A-2005/084799 describe a broad temperature range as being suitable for calcining zeolite Y in combination with binder. However, someone skilled in the art would be aware that the majority of such range is not suitable as a high temperature is suspected of breaking down the zeolitic structure. Therefore, someone skilled in the art would not seriously contemplate to apply the full temperature range of 300 to 800° C. mentioned in WO-A-2004/047988 or 300 to 850° C. mentioned in WO-A-2005/084799 but would only consider a relatively narrow range around the calcination temperature actually applied, i.e. 535° C.

Further, it was found that zeolite Y obtainable by the process of the present invention, differ from known zeolite Y in their infrared spectrum. Therefore, the present invention further relates to zeolite Y having a silica to alumina molar ratio of at least 10, the infrared spectrum of which carrier has a peak at 3700 cm$^{-1}$ but substantially no peak at 3670 cm$^{-1}$.

Furthermore, it was found that a specific kind of acidity of the zeolite Y modified by the present invention is less than the acidity of known zeolite Y. Therefore, the present invention also relates to zeolite Y having a silica to alumina molar ratio of at least 10, which carrier has an acidity as measured by exchange with perdeuterated benzene of at most 20 micromole/gram.

The calcination of the zeolite Y is carried out at a temperature of from 700 to 1000° C. The time during which the zeolite Y is calcined influences the exact temperature to be applied. Generally, the temperature is at most 850° C. At a calcination temperature of more than 900° C., loss of crystallinity was observed. The time during which the zeolite Y is calcined preferably is of from 20 minutes to 5 hours, more preferably of from 30 minutes to 4 hours. The time period to be applied depends on whether the oven is preheated or whether the temperature is increased while the catalyst carrier is being calcined. The time period preferably is at least 40 minutes, more preferably at least 50 minutes. Further, the time period is preferably less than 4 hours, more preferably less than 3½ hours. The temperature preferably is at most 850° C., more preferably at most 820° C., most preferably at most 800° C.

The calcination can be carried out in the presence or in the absence of steam dependent on the temperature applied. The steam partial pressure preferably is at most 0.04 bar at a temperature of from 700 to 800° C. The steam partial pressure preferably is at most 0.07 bar at a temperature of from 800 to 850° C. The steam partial pressure preferably is at least 0.05 bar, more specifically at least 0.07 bar at a temperature of from 850 to 900° C. The steam partial pressure preferably is at least 0.07 bar at a temperature of from 900 to 950° C. The steam partial pressure preferably is at least 0.08 bar, more specifically at least 0.1 at a temperature of from 950 to 1000° C. If steam is present, the steam partial pressure preferably is at most 0.5 bar, more specifically at most 0.4 bar.

It is preferred that the zeolite Y is calcined in the absence of amorphous binder.

Preferred zeolite Y materials for use in the present invention are zeolite Y having a silica to alumina ratio (SAR) of more than 10, especially an ultrastable zeolite Y (USY) or a very ultrastable zeolite Y (VUSY) of unit cell size ($a_o$) less than 2.440 nm (24.40 Ångstroms), in particular less than 2.435 nm (24.35 Ångstroms) and a SAR of more than 10, specifically of more than 10 up to 100. Suitable zeolite Y materials are known, for example, from European Patent Specifications Nos. 247 678 and 247 679, and WO 2004/047988.

Whilst USY and VUSY Y zeolites are preferred for use in the present invention, other Y zeolite forms are also suitable for use, for example the known ultrahydrophobic Y zeolites.

Preferred VUSY zeolite of EP-A-247 678 or EP-A-247 679 is characterised by a unit cell size below 2.445 nm (24.45 Ångstroms) or 2.435 nm (24.35 Ångstroms), a water adsorption capacity (at 25° C. and a p/p$_o$ value of 0.2) of at least 8% wt of the zeolite and a pore volume of at least 0.25 ml/g wherein between 10% and 60% of the total pore volume is made up of pores having a diameter of at least 8 nm.

Most preferred are the low unit cell size, high surface area zeolite Y materials described in WO-A-2004/050548. Such materials can be described as a zeolite Y having a SAR of greater than 13, a unit cell size in the range of from 24.10 to 24.40 Å, and a surface area of at least 875 m$^2$/g as measured by the BET method and ATSM D 4365-95 with nitrogen adsorption at a p/o values of 0.02, 0.03 and 0.04. Said materials can be prepared by a process which comprises a) providing a starting zeolite of the faujasite structure having a silica to alumina ratio of from 4.5 to 6.5 and an alkali level of less than 1.5% wt;

b) hydrothermally treating said starting zeolite at a temperature in the range of from 600 to 850° C., preferably 600 to 700° C. more preferably 620 to 680° C. and especially 630 to 670° C., and at a partial pressure of, preferably externally supplied, steam in the range of from 0.2 to 1 atmosphere for a time effective to produce an intermediate zeolite having a unit cell size of from 24.30 to 24.45 Å, being suitably in the range of from 0.5 to 5 hours, more suitably 1 to 3 hours;

c) contacting the intermediate zeolite with an acidified solution comprising an acid and optionally an ammonium salt under conditions effective to produce a high surface area zeolite having a unit cell size in the range of from 24.10 to 24,40 Å, a molar bulk silica to alumina ratio of greater than 13 and a surface area of at least 875 m²/g, thereby producing the high surface area zeolite; and d) recovering the high surface area zeolite.

Especially preferred high surface area materials have one or more of the following features:
unit cell size in the range of from 24.14 to 24.38, preferably from 24.24, more preferably from 24.30, to 24.38, preferably to 24.36, especially to 24.35 Å, and specifically in the range of from 24.14 to 24.33 Å;
a SAR in the range of from 20 to 100, preferably from 20 to 80, especially to 50;
surface area of at least 890, specifically at least 910 m²/g;
a micropore volume, as determined by nitrogen porosimetry using the t-plot method, also known as the t-method, using nitrogen as the adsorbate as described by Lippens, Linsen and de Boer, Journal of Catalysis, 3-32,(1964), of greater than 0.28 ml/g, suitably greater than 0.30 ml/g. Generally micropore volume will be less than 0.40 ml/g, suitably less than 0.35 ml/g. Herein micropores are pores having a diameter of less than 2 nm.

The present invention also relates to zeolite Y according to the present invention having an acidity as measured by exchange with perdeuterated benzene of at most 20 micromole/gram. This acidity more preferably is at most 15, more preferably at most 12, more preferably at most 10 and most preferably at most 8 micromole/gram.

The zeolites of the present invention find particular use as adsorbents, showing versatility in the type of material that can be absorbed. Adsorption capability even at low partial pressure of adsorbate has been found for both polar and non-polar materials. This makes the zeolites of the present invention very attractive for general adsorbency use and for use in pollution control. As polar materials, water and polar hydrocarbons may be mentioned. As mon-polar materials, non-polar hydrocarbons, such as aromatic hydrocarbons, for example benzene and toluene, may be mentioned. Accordingly, the present invention also provides for use as adsorbents of the modified zeolites Y according to the present invention, especially the zeolites Y of reduced acidity.

The present invention will now be illustrated by the following Examples.

EXAMPLES

In the Examples the following test methods have been used:
Unit cell size: Determined by X-ray diffraction using the method of ASTM D-3942-80.
Surface Area: Determined in accordance with the conventional BET (Brunauer-Emmett-Teller) method nitrogen adsorption technique as described in the literature at S. Brunauer, P. Emmett and E. Teller, J. Am. Chm. Soc., 60, 309 (1938), and ASTM method D4365-95. In the determinations quoted below, the results are given as a single point assessment taken at a nitrogen partial pressure of 0.03 following a high temperature pretreatment. (see also note below).
Silica to alumina molar ratio (SAR): Determined by chemical analysis; values quoted are 'bulk' SAR (that is to say the overall SAR) and not specifically the SAR of the crystalline framework.

Zeolite Y Preparation
The zeolite Y utilised in the catalysts of the present invention was prepared in accordance with the teaching of WO 2004/047988. The starting material used was low alkali content (<1.5%wt alkali oxide) ammonium form Y zeolites. These zeolites were prepared by one of two methods known in the art. While not meaning to be exclusive of other methods of achieving similar results, the examples were prepared by either the Cooper method (as described in U.S. Pat. No. 5,435,987) which involves $K^+$ ion exchange of Na form zeolite Y, followed by ammonium ion exchange, or by the Alafandi method (as described in U.S. Pat. No. 4,085,069) which involves ammonium exchange under autogenous superatmospheric pressure. The low alkali content ammonium form Y zeolite was steam calcined in one or two steps to create an ultrastable type Y zeolite. The steamed zeolites were then subjected to an acid-dealumination treatment consisting of a one step treatment with a combination of ammonium chloride and hydrochloric acid. The water content in the ion-exchange-dealumination treatment was generally sufficient to provide a zeolite slurry with from 5 to 25% anhydrous zeolite. Such variation is not believed to materially affect the results obtained.

The zeolite Y obtained had a silica to alumina molar ratio of 25, a unit cell size of 24.33 A and a surface area of 922 m²/g.

Infrared Spectrum
Additionally, the IR spectrums of the above catalyst carriers were measured with the help of a Biorad FTS 175 FT-IR spectrometer using a mercury cadmium telluride detector. The cell is equipped with a sample holder comprising 10 positions and samples have been measured as self-supporting wafers with a diameter of 18 mm, pressed from 25.3+/−0.1 mg zeolite powder at 3.5-4 Ton pressure. For the background measurement an open position of the sample holder has been used. Background and sample spectra have been measured by collecting 250 scans at 2 cm$^{-1}$ resolution. The spectrometer is flushed with nitrogen to minimize the interference of water vapor. After evacuating to less than $5\times10^{-4}$ mbar, samples have been activated in situ in a special heating zone by applying a temperature program of ramping to 450° C. at a rate of 10° C./min, with a hold time of 30 minutes at 450° C. Subsequently, samples have been cooled to 50° C. with 20° C./min. Then background and sample IR spectra have been measured.

H/D Acidity
After recording the above-mentioned spectra, the sample holder is slided back to the heating zone, and equilibrated at 50° C. for an additional 15 min, while the vacuum is maintained. H/D exchange has been performed in situ by letting 8-9 Torr of hexadeuterobenzene ($C_6D_6$) interact with the activated zeolite samples for 15 min at 50° C. followed by evacuation for 45 minutes to a target pressure of $5\times10^{-4}$ mbar (with a maximum of 1 hour). Then background and sample IR spectra have been measured.

To quantify the total amount of acidity, the IR spectra of the sample before (OH spectrum) and after (OD spectrum) contact with hexadeuterobenzene were compared as follows. The obtained OH spectrum was subtracted from the OD spectrum and baseline corrected. Then curve-fitting was performed with a predefined peak set for VUSY type materials and previously determined extinction coefficients.

Crystallinity
The crystallinity is measured by comparing with a highly crystalline VUSY reference by following the changes in peak broadening measured by XRD.

Example 1

Table 1 shows the properties of a sample of zeolite Y prepared as described above which has been calcined for 2 hours at 600° C.

TABLE 1

| Reference 1 | |
|---|---|
| Unit cell size (nm) | 2.433 |
| Crystallinity (%) | 99 |
| SAR | 24.95 |
| HD acidity (micromole/gram) | 175 |

Further samples of the freshly prepared zeolite Y also were calcined during 2 hours but now in the presence of steam and at a higher temperature as described in Table 2. The properties of the thus calcined zeolite Y are also shown in this Table.

TABLE 2

| | Reference 1 | Sample 1 | Sample 2 |
|---|---|---|---|
| Calcination T (° C.) | 600 | 900 | 950 |
| Steam (bar partial pressure) | na | 0.1 | 0.1 |
| Surface Area (m²/g) | 929 | 816 | 804 |
| Micropore Volume (cc/g) | 0.310 | 0.278 | 0.274 |
| Mesopore Volume (cc/g) | 0.186 | 0.189 | 0.192 |

The IR spectrums of the zeolite Y samples were measured as described above. It was found that samples 1 and 2 had a peak at 3700 cm$^{-1}$ but substantially no peaks at 3605 and 3670 cm$^{-1}$. The IR spectrum of Reference 1 was the opposite, i.e. it had peaks at 3605 and 3670 cm$^{-1}$ and no peak at 3700 cm$^{-1}$.

Example 2

In a similar fashion to Example 1, Table 3 shows the properties of a sample of zeolite Y prepared as described above and having been calcined for 2 hours at 600° C.

TABLE 3

| Reference 2 | |
|---|---|
| Unit cell size (nm) | 2.432 |
| Crystallinity (%) | 88 |
| SAR | 28.72 |
| HD acidity (micromole/gram) | 209 |

Further samples of the freshly prepared zeolite Y also were calcined during 2 hours in the absence of steam and at a higher temperature as described in Table 4. The properties of the thus calcined zeolite Y are also shown in this Table.

TABLE 4

| | Reference 2 | Sample 3 |
|---|---|---|
| Calcination T (° C.) | 600 | 850 |
| Surface Area (m²/g) | 859 | 834 |
| Micropore Volume (cc/g) | 0.284 | 0.274 |
| Mesopore Volume (cc/g) | 0.159 | 0.176 |

The IR spectrums of the zeolite Y samples were measured as described above. It was found that Sample 3 had a peak at 3700 cm$^{-1}$ but substantially no peaks at 3605 and 3670 cm$^{-1}$. The IR spectrum of Reference 2 was the opposite, i.e. it had peaks at 3605 and 3670 cm$^{-1}$ and no peak at 3700 cm$^{-1}$.

What is claimed is:

1. A process for preparing a modified zeolite Y which process comprises subjecting zeolite Y having a silica to alumina molar ratio of at least 10 to calcination at a temperature of from 700° C. to 1000° C. wherein (i) the steam partial pressure is at most 0.06 bar at a temperature of from greater than 700° C. to less than 800° C., (ii) the steam partial pressure is at most 0.08 bar at a temperature of from greater than 800° C. to less than 850° C., (iii) the steam partial pressure is at least 0.03 bar at a temperature of from greater than 850° C. to less than 900° C., and (iv) the steam partial pressure is at least 0.05 bar at a temperature of from greater than 900° C. to less than 950° C. or (v) the steam partial pressure is at least 0.07 bar at a temperature of from greater than 950° C. to less than 1000° C.

2. A process according to claim 1, in which process the zeolite Y has a silica to alumina molar ratio of more than 10.

3. A process according to claim 2, in which process the calcination is carried out during a time of from 20 minutes to 5 hours.

4. A process according to claim 3, in which process the zeolite Y before calcination has a bulk silica to alumina molar ratio of greater than 13, a unit cell size in the range of from 24.10 to 24.40 Å, and a surface area of at least 875 m²/g.

5. The process of claim 1 wherein the modified zeolite Y has a silica to alumina molar ratio of at least 10, the infrared spectrum of which has a peak at 3700 cm$^{-1}$ but substantially no peak at 3670 cm$^{-1}$.

6. A process according to claim 1, in which process the zeolite Y has an acidity as measured by exchange with per-deuterated benzene of at most 20 micromole/gram.

7. A process according to claim 6, in which process the zeolite Y has an acidity as measured by exchange with per-deuterated benzene of at most 10 micromole/gram.

8. A modified zeolite Y prepared by subjecting zeolite Y having a silica to alumina molar ratio of at least 10 to calcination at a temperature of from 700° C. to 1000° C. wherein (i) the steam partial pressure is at most 0.06 bar at a temperature of from greater than 700° C. to less than 800° C., (ii) the steam partial pressure is at most 0.08 bar at a temperature of from greater than 800° C. to less than 850° C., (iii) the steam partial pressure is at least 0.03 bar at a temperature of from greater than 850° C. to less than 900° C., and (iv) the steam partial pressure is at least 0.05 bar at a temperature of from greater than 900° C. to less than 950° C. or (v) the steam partial pressure is at least 0.07 bar at a temperature of from greater than 950° C. to less than 1000° C.

9. The modified zeolite Y of claim 8 wherein the zeolite Y has a silica to alumina molar ratio of more than 10.

10. The modified zeolite Y of claim 9, wherein the calcination of the zeolite Y is carried out during a time of from 20 minutes to 5 hours.

11. The modified zeolite Y of claim 10, wherein the zeolite Y before calcination has a bulk silica to alumina molar ratio of greater than 13, a unit cell size in the range of from 24.10 to 24.40 Å, and a surface area of at least 875 m²/g.

12. A zeolite Y having a silica to alumina molar ratio of at least 10, the infrared spectrum of which has a peak at 3700 cm$^{-1}$ but substantially no peak at 3670 cm$^{-1}$.

13. A zeolite Y having a silica to alumina molar ratio of at least 10, which zeolite Y has an acidity as measured by exchange with perdeuterated benzene of at most 20 micromole/gram.

14. The zeolite Y according to claim 13, which zeolite Y has an acidity as measured by exchange with perdeuterated benzene of at most 10 micromole/gram.

15. The modified zeolite Y of claim 8 having a silica to alumina molar ratio of at least 10, wherein the infrared spectrum of which has a peak at 3700 cm$^{-1}$ but substantially no peak at 3670 cm$^{-1}$.

16. A process according to claim 8, in which process the zeolite Y has an acidity as measured by exchange with perdeuterated benzene of at most 20 micromole/gram.

17. A process according to claim 16, in which process the zeolite Y has an acidity as measured by exchange with perdeuterated benzene of at most 10 micromole/gram.

18. A method of using a zeolite, wherein a modified zeolite Y prepared by subjecting zeolite Y having a silica to alumina molar ratio of at least 10 to calcination at a temperature of from 700° C. to 1000° C. wherein (i) the steam partial pressure is at most 0.06 bar at a temperature of from greater than 700° C. to less than 800° C., (ii) the steam partial pressure is at most 0.08 bar at a temperature of from greater than 800° C. to less than 850° C., (iii) the steam partial pressure is at least 0.03 bar at a temperature of from greater than 850° C. to less than 900° C., and (iv) the steam partial pressure is at least 0.05 bar at a temperature of from greater than 900° C. to less than 950° C. or (v) the steam partial pressure is at least 0.07 bar at a temperature of from greater than 950° C. to less than 1000° C. is used as an adsorbent.

19. The modified zeolite Y of claim 18 wherein the zeolite Y has a silica to alumina molar ratio of more than 10.

20. The modified zeolite Y of claim 19, wherein the calcination of the zeolite Y is carried out during a time of from 20 minutes to 5 hours.

21. The modified zeolite Y of claim 20, wherein the zeolite Y before calcination has a bulk silica to alumina molar ratio of greater than 13, a unit cell size in the range of from 24.10 to 24.40 Å, and a surface area of at least 875 m$^2$/g.

22. A method of using a zeolite, wherein a modified zeolite Y having a silica to alumina molar ratio of at least 10, the infrared spectrum of which has a peak at 3700 cm$^{-1}$ but substantially no peak at 3670 cm$^{-1}$ is used as an adsorbent.

23. A method of using a zeolite, wherein a modified zeolite Y having a silica to alumina molar ratio of at least 10, which zeolite Y has an acidity as measured by exchange with perdeuterated benzene of at most 20 micromole/gram is used as an adsorbent.

* * * * *